(12) United States Patent
Rodriques-Craig

(10) Patent No.: US 11,600,391 B1
(45) Date of Patent: Mar. 7, 2023

(54) CLASSIFYING AND GROUPING SERVICE DESCRIPTORS FROM HEALTH PROVIDER CHARGEMASTERS

(71) Applicant: Joanne Rodriques-Craig, Santa Clara, CA (US)

(72) Inventor: Joanne Rodriques-Craig, Santa Clara, CA (US)

(*) Notice: Subject to any disclaimer, the term of this patent is extended or adjusted under 35 U.S.C. 154(b) by 252 days.

(21) Appl. No.: 16/879,579

(22) Filed: May 20, 2020

Related U.S. Application Data

(60) Provisional application No. 62/853,281, filed on May 28, 2019.

(51) Int. Cl.
| | |
|---|---|
| *G16H 50/20* | (2018.01) |
| *G16H 70/20* | (2018.01) |
| *G16H 50/70* | (2018.01) |
| *G06F 40/40* | (2020.01) |
| *G16H 40/20* | (2018.01) |
| *G06F 16/28* | (2019.01) |
| *G06Q 30/02* | (2012.01) |
| *G06Q 30/0204* | (2023.01) |

(52) U.S. Cl.
CPC .......... *G16H 50/20* (2018.01); *G06F 16/285* (2019.01); *G06F 40/40* (2020.01); *G06Q 30/0204* (2013.01); *G16H 40/20* (2018.01); *G16H 50/70* (2018.01); *G16H 70/20* (2018.01)

(58) Field of Classification Search
CPC combination set(s) only.
See application file for complete search history.

(56) References Cited

U.S. PATENT DOCUMENTS

| | | | |
|---|---|---|---|
| 8,073,709 B2 | 12/2011 | Moreno | |
| 2006/0074712 A1* | 4/2006 | Jorgensen | G06Q 10/10 705/2 |
| 2008/0275724 A1* | 11/2008 | Moreno | G06Q 10/10 705/2 |
| 2015/0213219 A1* | 7/2015 | Antenen | G16H 50/30 705/2 |
| 2018/0081859 A1* | 3/2018 | Snider | G06F 40/44 |

(Continued)

OTHER PUBLICATIONS

Goldstein, Ira, et al., "Automated Classification of the Narrative of Medical Reports Using Natural Language Processing", ProQuest Dissertations and Theses, ProQuest Dissertations Publishing. (2011). (Year: 2011).*

(Continued)

*Primary Examiner* — Amber A Misiaszek
(74) *Attorney, Agent, or Firm* — GSS Law Group; Gregory S. Smith; Phillip Wagner

(57) ABSTRACT

Embodiments of a computer-assisted method classify service descriptors from chargemasters into national billing code equivalents for easy comparison of health provider prices. Medical libraries are attached and specialized rules are applied to augment service descriptors from chargemasters with supplementary medical information. A computer processor is configured to execute a text-based classifier and/or textual similarity metric to accurately associate service descriptors to national billing coding equivalents for service descriptors from different health providers. The disclosed embodiments form a comprehensive list of service descriptors grouped by national billing code equivalents and by textual similarity.

12 Claims, 17 Drawing Sheets

(56) References Cited

U.S. PATENT DOCUMENTS

2019/0034591 A1 1/2019 Mossin
2020/0372525 A1* 11/2020 Holmes .................. H04L 67/52

OTHER PUBLICATIONS

Author unknown, "pp. 1-5 from Chargemaster cms-1694-price-transparency-ucsfmc.pdf", original publication date unknown, pp. 1-5 representative of 2027 pages total, from spreadsheet file downloaded from University of California San Francisco Medical Center internet web site at https://www.ucsfhealth.org/about/pricing-transparency, file obtained on Mar. 4, 2020.

Author unknown, "2020dhsaddendum.pdf", pp. 1-25, Centers for Medicare and Medicaid Services, publication date Jan. 1, 2020, file obtained from internet web site at address https://www.cms.gov/apps/ama/license.asp?file=/files/zip/list-codes-effective-january-1-2020-published-december-2-2019.

* cited by examiner

| CPT Code | Service Descriptor | Price |
|---|---|---|
| 81170 | CHG ABL1 GENE ANLYS VARIANT KINASE DMN | 361.00 |
| 80400 | CHG ACTH STIM PANEL, ADR INSUFF | 141.00 |
| 85307 | CHG ACTIVATED PROT C (APC) RESISTNCE ASSAY | 97.00 |
| 82017 | CHG ACYLCARNITINES,QUANT,EACH SPEC | 194.00 |
| 87301 | CHG ADENOVIRUS AG, EIA | 49.00 |
| 86603 | CHG ADENOVIRUS, ANTIBODY | 47.00 |
| 87449 | CHG AG DETECT NOS, EIA, MULT STEP | 49.00 |
| 87450 | CHG AG DETECT NOS, EIA, SINGLE | 67.00 |
| | BUDESONIDE DR - ER 3 MG CAPSULE,DELAYED,EXTENDED RELEASE | 117.00 |
| | BUMETANIDE 0.25 MG/ML INJECTION SOLUTION: 05 mg (2 mL) | 57.00 |
| | ZIPPERED TORSO BRIEF 85 3XL SLACK (129871) | 143.78 |
| | ZIPWIRE .035 46-309B (61575) | 86.69 |
| C1769 | ZIPWIRE 0.025XI50CM BX/5 (65615) | 65.93 |
| C1769 | ZIPWIRE 38X1SO (114162) | 69.78 |
| C1769 | ZIPWIRESTRAIGHT 630-208B (111281) | 65.93 |

| Service Descriptor | Price |
|---|---|
| HS IV INF THER/PROPHY/DX INT<=1HR | $350 |
| HS IV INF THER/PROPHY /DX ADDL HR | 150 |
| HB IV INF ADDLSEQ NW DRG 1ST HR | $175 |
| HB IV INF THER/PROPHY/DX CNCRNT | $110 |
| HB IRRGTN IMPL VENOUS ACC DEV DRUG DEL SYS | $135 |
| HB IV INF PROL REQ PUMP >8HR | $350 |
| HB INJ IM/SUBQ THER/PROPHY/DX W PROCEDURE | $52 |
| HB INTRAVENOUS INFUSION PUMP | $350 |
| HBUC INJ IM/SUBQ THER/PROPHY/DX | $52 |
| HBUC IV INF HYDRATION INT 31MIN-1HR | $305 |
| HBUC IV INF HYDRATION EA ADDL HR | $130 |
| HBUC IV-INJ TX,PROPH,DX PUSH | $220 |
| HBUC INJ IV THER/PRPHY/DX SEQ NW | $135 |
| HB APPL ON-BODY INJECTOR FOR TIMED SUBQ INJECTION | $95 |
| HB SUBCUT INFUSION,THERAP/PROPH/DIAGNOST,INITIAL,1ST HR | $450 |

212 ⟋  ⟍ 202

CPT National Billing Code Equivalents:

The 6 main sections of Current Procedure Terminology (CPT) category I codes are:
1. Evaluation & Management Services (99201-99499)
2. Anesthesia Services (01000-01999)
3. Surgery (10021-69990)   — 214
4. Radiology Services ((70010-79999)
5. Pathology and Laboratory Services ((80047-89398)
6. Medical Services and Procedures (90281-99607)

210 ⟋     ⟍ 214

The 10 main sections of CPT category II codes are:
1. Composite Measures (00001F-0015F)
2. Patient Management ((0500F-0584F)
3. Patient History (1000F-1505F)
4. Physical Examination (2000F-2060F)
5. Diagnostic/Screening Processes or Results (3006F-3776F)
6. Therapeutic, Preventive, or Other Interventions (4000F-4563F)
7. Follow-up or Other Outcomes (5005F-52550F)
8. Patient Safety (6005F-6150F)
9. Structural Measures (7010F-7025F)
10 Nonmeasure Code Listing (9001F-9007F)

210 ⟋     ⟍ 214

CPT Category III codes are unclassified and new procedures:
1. 4-digit numeric codes followed by a T

Fig. 4

| CPT Code | Service Descriptor | Price |
|---|---|---|
| 86603 | CHG ADENOVIRUS, ANTIBODY | 47.00 |
| 87449 | CHG AG DETECT NOS, EIA, MULT STEP | 49.00 |
| 87450 | CHG AG DETECT NOS, EIA, SINGLE | 67.00 |
|  | BUDESONIDE DR - ER 3 MG CAPSULE,DELAYED,EXTENDED RELEASE | 117.00 |
|  | BUMETANIDE 0.25 MG/ML INJECTION SOLUTION: 05 mg (2 mL) | 57.00 |
|  | ZIPPERED TORSO BRIEF 85 3XL SLACK (129871) | 143.78 |

222  Appropriate National Billing Code Equivalent

224  No Appropriate National Billing Code Equivalent

Fig. 5

Apply Data Preprocessing Rules Specific to Domain
- Extension of word applied to specific context (medical procedure, test)
- Do not remove stop words, but change words or add context
- Extension of specialized use of numbers with context (eg. time for visits, measurement for tests, number of times a specific procedure is used)
- Extension and context applied to symbols (e.g. & -> and,+ --> or more)
- Removing unnecessary words, stopwords unique to this data, like "hc" or "hospital common"

| Service Descriptor | Terms used in the Procedure Term Matrix | Changes made to service descriptor |
|---|---|---|
| Hc office visit level iii new spec | office visit three new patient specialist | Change "iii" to three<br>New translates to new patient<br>Spec translates to specialist<br>Remove hc |
| CT abdomen w/o & w | ct abdomen with and without contrast | Note: "and", "to", and other stop words are not removed<br>w/o - without added contrast<br>w - with added contrast |
| Xr hip 2+ v | xray hip two or more views | Extension of words to add context<br>xr to xray<br>v to views<br>2+ to two or more |

Fig. 6

| Memorial Hospital (a) Charge Code | Service Descriptors | | Price |
|---|---|---|---|
| 1920933 | HG Glucose, CSF | | $108 |
| 1920938 | HG Tryptase level*3 | | $98 |
| *HC Glucose, CSF* | 1) Extending Medical Abbreviations *secondary* | (hospital common) glucose (colony stimulating hormone/cerebrospinal fluid) | |
| | 2) Adding Definitions *tertiary* | colony stimulating factor, act as hormones, locally secreted | |
| | 3) Adding Synonyms and Related Words *quaternary* | sugar; proteins, blood cells, glycoproteins central nervous system, brain, spinal cord vertebra | |
| *HC Tryptase level*3* | 1) Extending Medical Abbreviations *secondary* | (hospital common) tryptase (three measurements) | |
| | 2) Adding Definitions *tertiary* | enzyme released from mast cells | |
| | 3) Adding Synonyms and Related Words *quaternary* | blood, normal immune response, allergy | |

Fig. 7

| Word | Procedure | Anatomy | Medical Device | ... | Not Found |
|---|---|---|---|---|---|
| (glucose) 228 | xray | brain | endoscope | | |
| | ct | esophagus | fine needle | | |
| | ultrasound | lungs | balloon | | |
| | test | blood | cholangiopan-creatography | | |
| | mra | (glucose) 232 | catheter | | |
| | mri | thorax | suture | | |
| | endoscopy | bladder | dressing | | |
| | visit | liver | nebulizer | | |
| | ... | ... | ... | | |

Table labeled 230; Anatomy column indicated.

Fig. 8

Words from Service Descriptors

| Category | glucose | bleed | sugar | visit | ... |
|---|---|---|---|---|---|
| Anesthesia | 0 | 0 | 0 | 0 | |
| Surgical Procedures | 0 | 1 | 0 | 0 | |
| Pathology | 1 | 1 | 1 | 0 | |
| Laboratory | 1 | 1 | 0 | 0 | |
| Medicine | 0 | 0 | 0 | 0 | |
| Radiology | 0 | 0 | 0 | 0 | |
| Evaluation and Management | 0 | 0 | 0 | 1 | |
| Category II | 0 | 0 | 0 | 0 | |
| Category III | 0 | 0 | 0 | 1 | |
| No CPT | 0 | 0 | 1 | 1 | |

Fig. 9

Variable Importance
Factor (V)

Procedure Frequency
Matrix (F)

Match Matrix
(M)

Match score for
CPT code i $$(5)\ Y = \begin{pmatrix} V\_1 & V\_2 & \ldots & V\_k \end{pmatrix} \times \begin{pmatrix} F\_1 \\ F\_2 \\ \ldots \\ F\_k \end{pmatrix} \times \begin{pmatrix} M\_1 & M\_2 & \ldots & M\_k \end{pmatrix}$$

$$(6)\ Y = \text{Max} \sum_{i=1} \underbrace{V\_1*F\_1*M\_1 + V\_2*F\_2*M\_2 + \ldots + V\_k*F\_k*M\_k}_{\text{Match Score}}$$

(7) Variable Importance Factor (V) =

{Weight based on extender type (primary, secondary, etc.)} × {Weight based word type - procedure, anatomy, medical device, etc.} × {Weight frequency of word in the national billing code equivalent versus category etc.}

Fig. 11

| Service Descriptor / 204 | National Billing Code Equivalents / 212 | Probability / 216 |
|---|---|---|
| hc colonoscopy | 45378. Colonoscopy, flexible; diagnostic, inducting collection of specimen(s) by brushing or washing, when performed. | 80.00% |
| | 45379. Colonoscopy, flexible; with removal of foreign bodies | 15.00% |
| | 45380. Colonoscopy, flexible; with biopsy, single or multiple | 5.00% |
| | 45381 | 0.00% |
| | 45382 | 0.00% |
| | 45388 | 0.00% |
| | 45384 | 0.00% |

| Health Provider 218 | Service Descriptor 204 | CPT Code 202 | Price 206 |
|---|---|---|---|
| Hospital Q | HC Glucose Test | 82947 | $67.00 |
| Hospital R | Glucose | 82947 | $72.00 |
| Hospital S | Glucose Assay | 82947 | $98.00 |
| Lab T | Glucose 1 | 82947 | $147.00 |
| Clinic U | Glucose Basic | 82947 | $250.00 |

Fig. 14

| Health Provider 218 | Service Descriptor 204 | New Service Designation 226 | Price 206 |
|---|---|---|---|
| Hospital Q | HC Room & Board | Description: Room and Board (basic per day) Code: 10098976 | $1250 |
| Hospital X | Room and Board basic | 10098976 | $1375 |
| Hospital Z | R&B non-surgical | 10098976 | $2050 |
| Hospital S | Room and Board non-ICU | 10098976 | $2055 |
| Surgical Center P | Room and Board (rate/day) | 10098976 | $2250 |

Fig. 16

Price List for ct scan of the pelvis with contrast or dye

| Sort Order: | Price |
|---|---|
| | Provider Name |
| | Lowest to Highest |

Category: Radiology and imaging    CPT: 72193

Please call health care providers billing departments to verify price.

Showing: 2 of 18 results

ABC Medical Foundation
Santa Clara Center
tel: (408) 123-4567
addr: 123 Main St

CPT: 72193

| Public List Price | Avg Insurer Adj Price | Estimated Cash Price |
|---|---|---|
| $763.00 | $534.10 | $534.10 |

XYZ Imaging
Los Gatos
tel: (408) 321-7654
addr: 222 Vine Ave

CPT: 72193

| Public List Price | Avg Insurer Adj Price | Estimated Cash Price |
|---|---|---|
| $814.43 | $570.10 | $276.34 |

US 11,600,391 B1

CLASSIFYING AND GROUPING SERVICE DESCRIPTORS FROM HEALTH PROVIDER CHARGEMASTERS

FIELD OF THE INVENTION

The present work relates to chargemasters or health provider pricing lists for services, procedures, medications, supplies, fees and medical devices from hospitals, clinics, labs, radiology centers, surgery centers, emergency, urgent care, ambulatory, dental, optometry and pharmacies.

BACKGROUND

On Jan. 1, 2019, the Centers of Medicare and Medicaid Services (CMS) required that all hospitals nationwide publish chargemasters for medical services in a machine-readable format. A chargemaster is a list of prices for all services a health provider offers. The services can include procedures, medications, supplies, professional and facilities fees. While this rule applies solely to hospitals, other health providers can voluntarily disclose their chargemasters. A health provider is a hospital, clinic, laboratory, radiology center, surgery center, emergency room, urgent care, ambulatory services, dental practice, optometry practice, pharmacy or other provider of health services. Many services, but not necessarily all, have a national billing code equivalent associated with them. National billing code equivalents are systems of coding used to categorize chargemaster items into billable services defined across health providers. The national billing code equivalents include the following: Current Procedure Terminology (CPT), the Hospital Common Procedure Coding System (HCPCS), International Classification of Diseases (ICD-10), and the Disease-Related Groups (DRG).

Health providers use national billing code equivalents to bill insurance companies, government health plans and uninsured patients for services. Use of the national billing code equivalents is nearly universal, but national billing code equivalents are not included in many chargemasters, making prices difficult to compare between health providers. Each item in the chargemaster has a service descriptor and a price. A service descriptor refers to a brief explanation of the service provided by a health provider. While national billing code equivalents are the same across providers, a provider's service descriptor greatly varies. Accuracy of assigning national billing code equivalents to service descriptors with a human expert is low, resulting in the inability for healthcare consumers to compare similar services at multiple health providers.

SUMMARY

The method and process herein use at least one classifier to group service descriptors into national billing code equivalents or, in the case of no national billing code equivalent, uses at least one textual similarity metric to group service descriptors to one another. A textual similarity metric is a metric that approximates similarity between two strings or groupings of words and/or other characters. Using textual similarity metrics allows for a consistent estimation of similarity.

In the preferred embodiment, service descriptors are augmented by extending the descriptions to include auxiliary words and classified using a two-stage machine learning classification approach, to classify service descriptors into categories and then to classify service descriptors into national billing code equivalents, using a variable importance factor, which weights types of words, extenders, and varied measurements of word frequencies. Service descriptors that have no national billing equivalent are then grouped to other service descriptors based on at least one textual similarity metric. The additional services are then codified to build a comprehensive list of billable services at American health providers.

Chargemasters are not currently used to compare prices between health providers because of the difficulty of interpreting service descriptors by human experts and health consumers. The current method of searching chargemasters with the aid of billing experts is severely limited because of the brevity, complex medical jargon, the vast number, the high level of similarity and the large variance across health providers of service descriptors. Disclosed herein is a process and method for classifying billing code descriptions, consisting of a two-stage classification approach, resulting in a much higher level of accuracy compared to a human expert for classification of service descriptors into national billing code equivalents and to one another.

BRIEF DESCRIPTION OF DRAWINGS

FIG. 2 is an example chargemaster with service descriptor, price, and national billing code equivalents;

FIG. 3 is an example chargemaster dataset with service descriptor and price (without national billing code equivalents);

FIG. 4 shows a listing of preferred CPT codes;

FIG. 5 shows a chargemaster with national billing code equivalents, where service descriptors within are grouped into 'appropriate' or 'no appropriate' national billing code equivalents;

FIG. 6 is a diagram of the method to preprocess service descriptors with examples;

FIG. 7 is a example of the method to extend service descriptors with the use of medical libraries;

FIG. 8 is an example of how words in service descriptors are categorized by exact correspondence into a word type category;

FIG. 9 is an example Procedure Term Matrix which is used to classify service descriptors into national billing code equivalent categories;

FIG. 11 is the diagram of classifying service descriptors into national billing code equivalents;

FIG. 13 denotes the embodiment where service descriptors are assigned by likelihood of belonging to national billing code equivalents;

FIG. 14 is an example of how service descriptors without 'appropriate' national billing code equivalents or service descriptors from chargemasters without national billing code equivalents classified into the 'no CPT' are grouped together;

FIG. 16 is a schematic diagram of a healthcare consumer interface to search for providers with the lowest price by service, and further represents an example of information resulting from operation of an embodiment optionally displayable on a computer display;

DESCRIPTION

Figure 1:
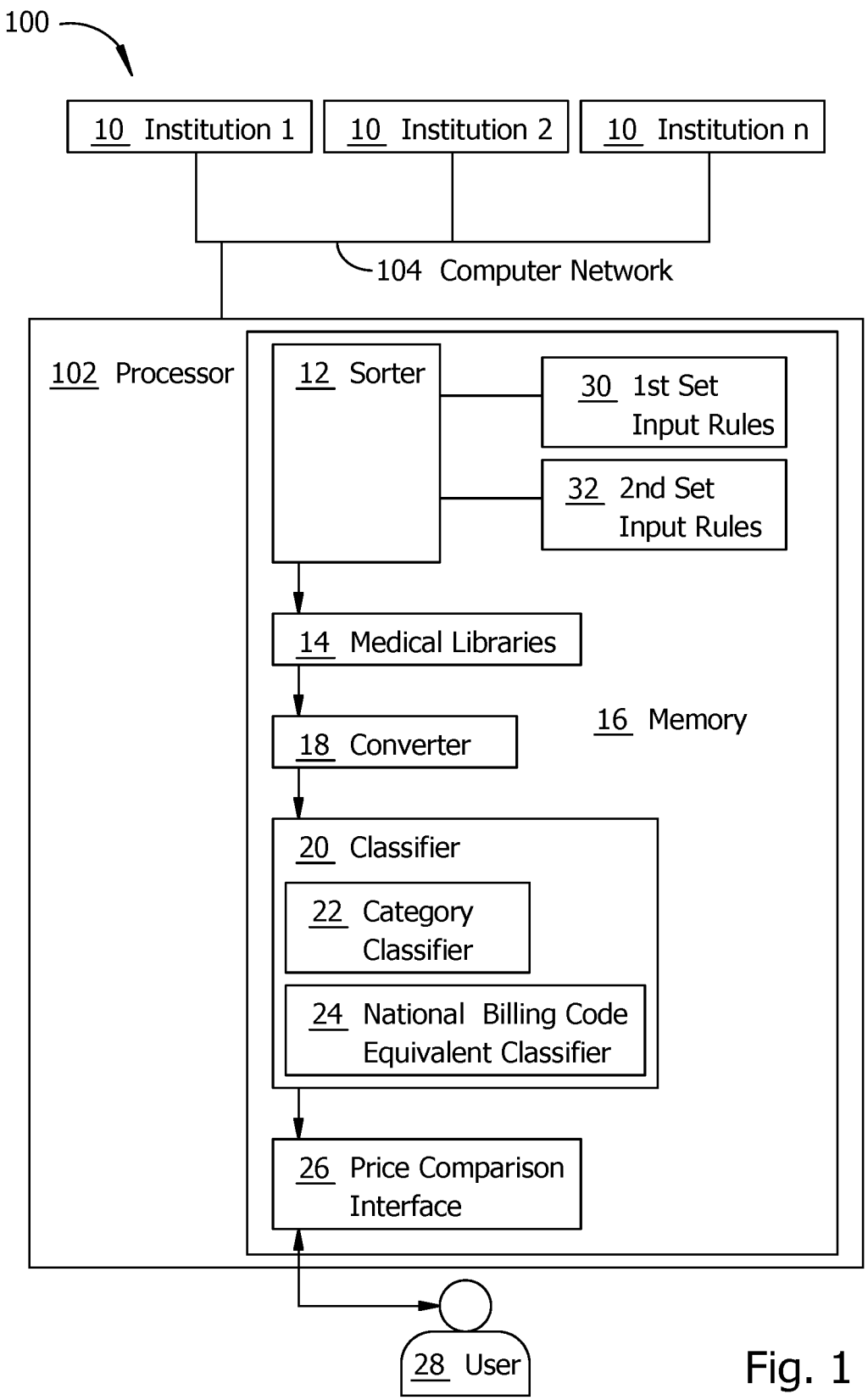
FIG. 1 is the elements diagram for the preferred embodiment of system of finding identical service descriptors and/or grouping service descriptors from health provider chargemasters.

The computer system and method described herein classifies service descriptors from multiple health providers to their national billing code equivalents or groups service descriptors without national billing code equivalents to each other by a textual similarity metric. FIG. 1 is a schematic diagram of an example embodiment 100 showing examples of operational elements for classifying and grouping service descriptors to allow price comparison of services. The example embodiment 100 categorizes service descriptors according to the most relevant CPT codes 202. A CPT code 202 is a five-digit alphanumeric code used to describe tests, surgeries, evaluations, and other medical procedures. A CPT code 202 available on a list of CPT codes managed by the American Medical Association will be referred to herein as a preferred CPT code 214. The example embodiment 100 includes a computer processor 102 configured to provide a comprehensive listing of services offered by health providers, including services without preferred national billing codes equivalents. In some embodiments 100, the computer processor 102 is implemented in semiconductor hardware. As used herein, a preferred national billing code equivalent is a billing code found in lists maintained by the Hospital Common Procedure Coding System (HCPCS), International Classification of Diseases (ICD-10), the Disease-Related Groups (DRG), and CPT codes from the American Medical Association. This method can aid in demonstrating which commonly used procedures are not included in preferred national billing code equivalents and document which services of any type are commonly used across regions or hospital systems. The computer-assisted system herein is effective for processing tens of millions of service descriptors, far faster, and more consistently and accurately than could reasonably be expected to be performed by a human expert in interpreting and comparing CPT codes and service descriptors.

Institutions 10 can include hospitals, clinics and other health providers, governmental organizations and other aggregators of health data. Health providers have chargemasters with 10,000-120,000 unique services, procedures, medications and supplies. Chargemasters are not comparable across providers because service descriptors and prices vary from one health provider to the next. Chargemasters are available on institutions' websites in online data stores. An online data store is an internet repository for storing and managing collections of data. Chargemasters can be found in a variety of machine-readable formats, i.e. CSV, EXCEL, JSON, XML, and non-easily machine-readable formats, i.e. PDF, online calculators or webpages. If not in a machine-readable format, chargemasters are converted into a machine-readable format with a computer program or with a human expert.

Chargemasters have a column of service descriptors. For example, the procedure descriptor "hc room and board" which indicates a charge per night for staying in a standard hospital room. Another example of a procedure descriptor is "hc glucose, csf" denoting a glucose test in the lab. Chargemasters have a price column, with charges for the procedure described.

Chargemasters from online data stores are classified with the first set of input rules 30. The first set of input rules 30 is a set of guidelines that separate chargemasters with national billing code equivalents and those without national billing code equivalents. FIG. 2 shows an example chargemaster 200 with national billing code equivalents 212. Each of the national billing code equivalents 212 are represented by a CPT code 202. FIG. 2 further shows examples of service descriptors 204, prices 206, and missing CPT codes 208. FIG. 3 shows an example chargemaster 200 without national billing code equivalents. Here is an example of the first set of input rules to determine if a chargemaster has a national billing code equivalent: (1) has a numeric column, (2) has greater than 10% of entries in either of the following two categories: (a) has a five digit numeric code or (b) has a four digit numeric code followed by one accepted alphabetic character such as F, T or U, and (3) entries have textual equivalence to preferred CPT codes 214 over 85% of the time. Textual equivalence as used herein refers to identical character-by-character sequences in two or more text strings. A text string containing CPT codes 202, service descriptors 204, or other information may be said to have a match in another text string when all of the characters of one of the strings, including letters, symbols, non-English-language characters, numbers, punctuation, and whitespace, are found in identically the same character-by-character sequence in the other text string. Character fonts, character colors, the presence or absence of underlining, bold type, italics, highlighting, and other font effects are not required to be identical. FIG. 4 shows the list of preferred CPT codes 214. If a column exists that meets the first set of input rules, then the chargemaster 200 is classified to have national billing code equivalents 212. In this case, the national billing code equivalent is CPT, but input rules could vary to find other national billing code equivalents such as DRG, ICD-10, HCPCS. If not, then the chargemaster 200 is classified to be without national billing code equivalents 212. Most chargemasters do not include national billing codes equivalents. As many as all chargemasters or as few as none contain national billing code equivalents, while the proportion of 5% to 30% is typical. FIG. 4 further illustrates an example of specifications 210 for national billing code equivalents. In the example of FIG. 4, the specification 210 refers to descriptive text associated with one or more preferred CPT codes 214, expressed in the example as a range of CPT code values. For example, the specification 210 for CPT codes in a range from 90281 to 99607 is "medical services and procedures". Preferred specifications 210 and preferred CPT codes 214 may be obtained from the American Medical Association.

The second set of input rules 32 is applied to chargemasters with national billing code equivalents. Here is an example of the second set 32 of input rules: (1) if the national billing code equivalent is blank or does not have a preferred national billing code equivalent, the service descriptor 204 is assigned to have 'no appropriate' national billing code equivalent and (2) If the national billing code equivalent is found to have a preferred national billing code equivalent, the national billing code equivalent 212 is assigned to that service descriptor. The service descriptor is deemed to have an 'appropriate' national billing code equivalent. FIG. 5 shows example service descriptors 204 and prices 206 in the chargemaster 200 with national billing code equivalents 212 of an 'appropriate' national billing code equivalent 222 and 'no appropriate' national billing code equivalent 224. In the example of FIG. 5, the example national billing code equivalents 212 correspond to CPT codes 202. Each service descriptor 204 has an associated price 206. For instance, service descriptor 'Room and Board' has no CPT code associated with it. On average, approximately 50% of service descriptors in chargemasters with national billing code equivalents contain 'appropriate' national billing code equivalents 222. These services without an 'appropriate' national billing code equivalent 224 exist in chargemasters without national billing codes equivalents as well, but must be found through the methods herein.

Medical libraries and dictionaries are attached and health provider procedure descriptions are preprocessed 14 in the converter 18. Medical libraries consist of anatomical lists, medical device lists, medical abbreviations, medical documents, medical dictionaries and medical encyclopedias, and other medical reference texts found in reference sites like MedlinePlus, WebMD and other online medical websites. Service descriptors have certain peculiarities including: (1) use of medical abbreviations, shortened representations of longer phrases or words, and medical jargon, (2) unconventional usage of numbers, (3) unique wording styles, (4) medical coding intricacies including ordering, (5) charge and revenue codes, and (6) unique formatting within hospital systems and provider type. Medical libraries are used to extend service descriptors in chargemasters. Medical libraries are used to extend medical abbreviations, short hand and medical jargon and add context to unconventional usage of numbers in service descriptors. The methods herein address the unique elements of this particular data and are adapted to chargemasters within the American healthcare industry.

Since the service descriptors compress the core information that can be used for classification, service descriptors are augmented by preprocessing and extending them to increase the information. Preprocessing rules are only carried out on primary (original descriptor) and secondary terms (abbreviations). Preprocessing rules and examples are given in FIG. 6. Each preprocessing rule implements a specific conversion and/or replacement of a string of text with another string of text, such as a rule for changing "w/o" to "without", "hc" to "hospital common", and so on. An embodiment 100 will in general contain many such rules, one rule for each abbreviation or shorthand representation found in descriptors. Previously-known data preprocessing techniques often include removal of stopwords. However, in contrast to many previously known data processing techniques, traditional stopwords are not removed by an embodiment 100 because many stopwords add useful information. For instance, the stopwords 'and' and 'with' can add information about what's included in a procedure and how it should be coded. Instead, domain-specific stop words are preferably removed, such as 'hc' and 'hospital common' because such domain-specific words provide little information about how to classify a given service descriptor, where "domain" refers to a data source such as an institution from which a chargemaster has been obtained. Next, words are stemmed. Stemming refers to shortening a word to its base form and is a common data cleaning technique. Next, abbreviations, numbers and letters are extended and context is added. There are a large set of rules to extend commonly used abbreviations, numbers and letters that occur in service descriptors. Many medical abbreviations have a number of potential meanings in different contexts. Therefore, a large set of rules are applied such that abbreviations, numbers and symbols are appropriately extended to reflect these different meanings in different categories or contexts. For example, the word "v", if "xray" is present, translates to "views". When "v" occurs with "visit" or in the Evaluation and Management CPT category, "v" is translated to "level 5". Preprocessing includes adding appropriate extensions to all numbers, roman numerals, letters and symbols with category context.

Since chargemaster service descriptors are brief, service descriptors are extended with four types of additional information from medical libraries, termed primary, secondary, tertiary and quaternary. The first designation is the primary descriptor itself. An example is "hc glucose, csf". The primary term is "glucose." The secondary word type is abbreviations added to the service descriptor. For instance, in "hc glucose, csf", "hc" adds "hospital common" and "csf" has two potential medical abbreviations which are both added, "cerebrospinal fluid" and "colony stimulating hormone." The secondary terms are "hospital common", "cerebrospinal fluid" and "colony stimulating hormone." The third type is definitions of objects in the service descriptor or secondary terms. One attached definition for this example is "sugar" as a definition of glucose; "sugar" would be a tertiary term. The fourth word type is synonyms or diagnoses for a particular test, procedure, or other medical service. For the descriptor "hc glucose, csf", synonyms added are "brain" or "spinal cord" and "meningitis" for diagnoses. This example is denoted in FIG. 7.

Medical libraries are also used to identify the word type of each word in a service descriptor. The word types include, but are not limited to the following: procedure, anatomy, medical device, measurement or count, level, time interval or none. These elements were created based on the structure of service descriptors, which usually have a "procedure" on some part of the human "anatomy" occasionally with a "medical device" for a "length of time", "number of times", "interval" or "measurement" depending on the service. None of these elements are mandatory, but are often included in descriptions. As word lists have thousands of entries, using a computer program, words are classified by exact correspondence to lists for each of the word types in the order above. For instance, the word 'glucose' would be in word type anatomy. First, a 'procedure' word list would be searched, but since 'glucose' is not on a 'procedure' word list a classification to the procedure word list. Next, the 'anatomy' word list would be searched. Since 'glucose' is on the 'anatomy' word list, then it is classified in the 'anatomy' word type. FIG. 8 depicts an example of this process, marking with an oval "glucose" under the "Word" column as an example of a word whose word type is to be determined 228, marking "glucose" again under the "Anatomy" column to indicate a successful search for an exact character-by-character equivalent word 232, leading to assignment of "Anatomy" as the word type 230 for "glucose" 228.

In the preferred embodiment, after the service descriptors are augmented by the converter 18, service descriptors with national billing code equivalents are used to train at least one classifier 20 to assign health provider descriptors to national billing codes 212. A classifier accepts as inputs words from service descriptors, and uses them to classify an output, for example a national billing code equivalent 212 or coding category. Training is when classified data is used, for example chargemasters with national billing code equivalents 212, to build a model to classify new data into the appropriate category, in this case national billing code equivalents. The new data which the trained classifier is applied to is called test data. In this example, the test data is chargemaster service descriptors without national billing code equivalents. In the preferred embodiment, a two-stage process is employed, where service descriptors are classified into categories 22 and then classified into national billing code equivalents 24. While the process can be done in one-stage, the two-stage process approach was employed in the preferred embodiment to lower the processing load. In another example embodiment, this process can be done in a one-stage classification model. In other embodiments many individual classification models could be used, such as one for each billing code.

In the preferred embodiment, service descriptors are classified into a coding category 22. There are at least four different types of national billing code equivalents, each has their own categories. For CPT code, categories include: 'Anesthesia', 'Surgical Procedures', 'Pathology', 'Laboratory', 'Medicine', 'Radiology', 'Evaluation', 'Category II', Category III', and 'No CPT' code. All national billing code equivalents have procedures that are not categorized within that billing code. The 'no appropriate' national billing code equivalents, in chargemasters without national billing code equivalents, are defined as 'No CPT'. The words and phrases in service descriptors from chargemasters with national billing code equivalents are used to create a Procedure Term Matrix (PTM). The PTM is a matrix where the rows correspond to the categories and each column is a word in the augmented service descriptors from chargemasters with national billing code equivalents. FIG. 9 shows a sample PTM. As the PTM can be large and unwieldy, information compression approaches can be applied such as Principal Component Analysis (PCA) or Multiple Correspondence Analysis (MCA) which is the analog to PCA for boolean variables. In other embodiments, other features can be added to the example procedure term matrix to be used in the model.

Figure 10:
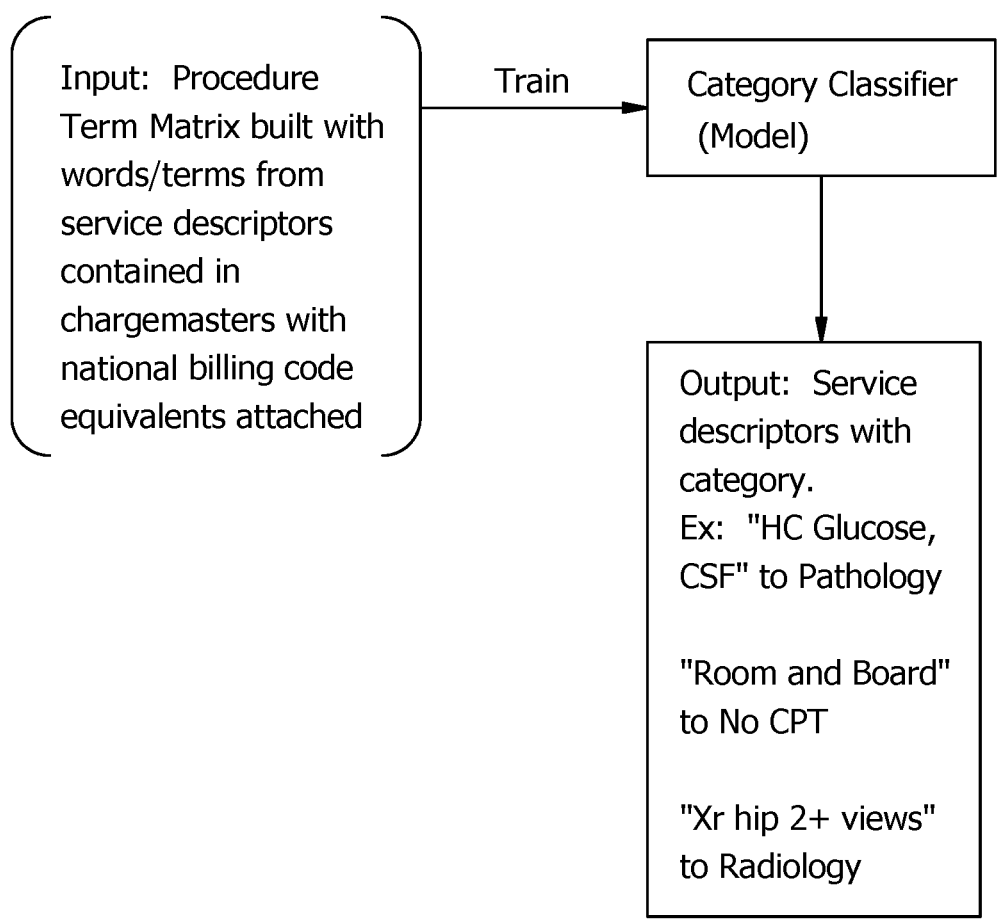
FIG. 10 is an example of the process to categorize service descriptors into national billing code equivalent categories.

The service descriptors from chargemasters, with national billing code equivalents, are used to build at least one text-based classification model to predict the category for each service descriptor. In the preferred embodiment, a multiclass support vector machine is used to classify service descriptors into categories, which is built using the PTM created from the service descriptors from chargemasters with national billing code equivalents. The output is the category of the descriptor. FIG. 10 shows the process of classifying service descriptors into categories. For example, procedure description "hc glucose, csf" is classified into Pathology. When classified into national billing code equivalents, only codes in the Pathology category are considered or CPT codes between 80047-89398.

Example embodiments for national billing code equivalent classification include three matrices for classifying service descriptors into their national billing code equivalents 24. Service descriptors from chargemasters with national billing code equivalents are used to build the Variable Importance Factor (V) Matrix, Frequency Matrix (F), and Match Matrix (M) to calculate match scores between a service descriptor and a national billing code equivalent in the classified coding category. In the mathematical formulations (1) to (4) below, representing some operations performed by an embodiment 100, the output Y is the match score matrix, which is a matrix where each row denotes a match score for every national billing code equivalent in a category. N is the number of preferred national billing code equivalents in a category. L is the number of words in each service descriptor, i is the service descriptor to be classified and k is a word in the augmented service descriptor. M is the boolean matrix, where 1 denotes a textual equivalence between the descriptor and the preferred billing code definition and 0 denotes no textual equivalence.

V is a matrix of the variable importance parameters unique to each word, including extender type, word type, and word frequency in the national billing code equivalent versus the category.

$$Y = \Sigma i=_1 \Sigma_{k=1} V_{i,k} * F_{i,k} * M_{i,k} \qquad (1)$$

$$V_{i,k} = v_{1,i,k} * v_{2,i,k} * v_{3,i,k} \qquad (2)$$

$M_{i,k}=1$ when a descriptor word is equivalent to a word in a billing code description  (3)

$M_{i,k}=0$ when a descriptor word does not have an equivalent word in a billing code description  (4)

The parameter weights, v, for V are built using a subset of service descriptors from chargemasters with national billing code equivalents. The first weight is for extender type (primary, secondary, tertiary, quaternary). The second factor is the weight for the word type in the service descriptor. The process of converting words into word types is described previously. The final factor is based on the frequency of the word in service descriptors versus the average frequency of that word in the national billing code equivalent category. For instance, the word 'glucose' appears in 1 out of 10 service descriptors in the national billing code equivalent 82945 and in 1 out of 100 service descriptors in the Pathology, the factor is 10 in this case. If a word does not appear in a subset of service descriptors of chargemasters with national billing code equivalents, the word receives a one. FIG. 11 illustrates in equations (5), (6), and (7) members of three matrix components and how they are used to calculate match scores.

The F, which measures the frequency of a word in a national billing code equivalent, is built with a subset of service descriptors from chargemasters with national billing code equivalents. For instance, 'glucose' occurs four hundred times out of five hundred service descriptors in national billing code equivalent 82945. If a word does not occur in any service descriptors, the word receives a one. The match matrix M is used to connect a service descriptor to a description from a preferred national billing code equivalent. The preferred descriptions are a set of descriptions (short-form, long-form, medium-form, consumer, provider) for national billing code equivalents managed by the organization responsible for creating and maintaining those codes. In the case of CPTs, this set of preferred descriptions are put out by the American Medical Association as previously explained. The matrix has a Boolean value of one when a word in the service descriptor is identical to any word in the preferred descriptions, where two or more identical words have identical character sequences. Together, the V, F, and M matrices are used to calculate match scores. Each service descriptor will have a match score for every national billing code equivalent in the category. For instance, "hc glucose, csf" will have match scores for all billing codes in Pathology or CPT codes between 80047-89398.

Figure 12:
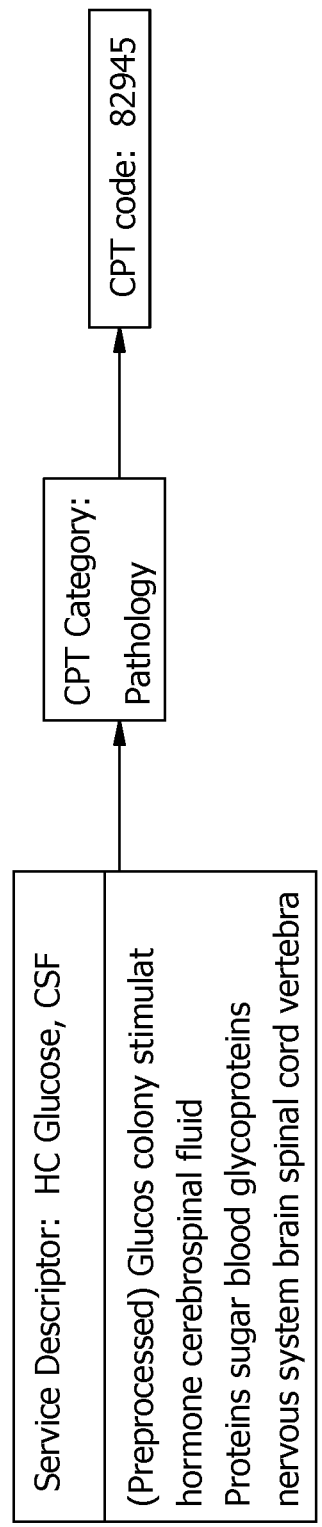
FIG. 12 is a flowchart of how a service descriptor from a chargemaster, without national billing code equivalents, is classified into a national billing code equivalent.

The following is an example of how to calculate the component of the match score for the word 'glucose' in the 'hc glucose, csf' service descriptor for billing code 82945. For instance, 'glucose' occurs four hundred times in the billing code category 82945 in a subset of chargemasters with 'appropriate' national billing code equivalents. To calculate the variable importance factor for 'glucose', the extender type 1 (primary has a factor of 1) is multiplied by word type 5 (factor for word type 'anatomy') by 400 (frequency), and by 1 (as it occurs in the long form of the formal description of billing code 82945). The summation for the word 'glucose' is 2,000 in the national billing code equivalent 82945. Similarly to how the component for 'glucose' is calculated, the process is completed for all words in the augmented service descriptor 'hc glucose, csf'. The process is carried for every national billing code equivalent within the classified category. The national billing code equivalent associated with the highest match score is the national billing code equivalent that the service descriptor belongs to. FIG. 12 depicts the process of categorizing a service descriptor into category and then into its national billing code equivalent.

The variable importance matrix Vis crucial in determining the correct national billing code equivalent in a category. The word type is particularly crucial in selecting between two similar national billing code equivalents. In Radiology, the word 'two' is classified as a 'measurement' word type. Measurement word types are particularly important in the Radiology category to differentiate between national billing code equivalents. For instance, 'x-ray chest two views' is in a different national billing code equivalent than 'x-ray chest four views'. Measurement word types are weighted less highly in the Surgical Procedures, than in Radiology, while other word types like medical devices are more highly weighted. Finally, the frequency of a word in a national billing code equivalent versus the average frequency of a word in the category is very important for words that occur commonly in a category like the word 'views' in Radiology and must be properly downweighted. In other embodiments, other relevant factors can be included into the variable importance factor to better classify service descriptors.

In a further embodiment, a loss function can be added to penalize longer service descriptors. A loss function is a function that maps variable(s), in this case the length of the service descriptor, to a real-valued number associated with some "cost" associated with that variable outcome. Service descriptors, which contain large numbers of words will have a higher match score on average than shorter service descriptors. To correct for this bias in the classification approach, a loss function can be added that penalize longer service descriptors or other variables in the formulation.

In the preferred embodiment, all national billing code equivalents with match scores above a threshold 'degree of confidence' are attached to a service descriptor, otherwise the service descriptor is left unattached. Attachment denotes that service descriptor belongs to the set of service descriptors in that national billing code equivalent. The threshold is a unique parameter that is calculated from classified data, by examining the threshold needed to find the correct billing code with high accuracy. In practice, 'degree of confidence' is a classification accuracy rate greater than 95%, determined on a subset of service descriptors from chargemaster data with an 'appropriate' national billing code equivalent. If there is a tie which is above the threshold 'degree of confidence', then a service descriptor is attached to all national billing code equivalents. With a defined threshold, the method can be used to remove service descriptors that have not been successfully classified. The removed service descriptors may then be classified by similarity or remain unclassified.

A further example embodiment attaches service descriptors to national billing code equivalents by probability. By defining the attachment based on probability, the process allows for classification to multiple national billing code equivalents. All match scores above the threshold 'degree of confidence' are included. The probability is determined by each match score over the sum of all match scores above the threshold 'degree of confidence'. For instance, "hc glucose, csf" might have a 90% probability of being attached to the national billing code equivalent of 82945 (match score 900, calculated by 900/1000) and a 10% probability of being attached to the national billing code equivalent of 82947 (match score 100, calculated by 100/1000). FIG. 13 depicts how service descriptors 204 are assigned by probability 216 to different national billing code equivalents 212.

In the preferred embodiment, all the remaining service descriptors not attached to a national billing code equivalent, which could be as many as all service descriptors or as few as none, are grouped to one another using at least one textual similarity metric. A textual string is a string of alphanumeric characters, which usually can be interpreted as words. Two strings can be fed into a textual similarity metric, which has some criteria for determining how 'close' these strings are to one another. A common textual similarity metric is the Levenshtein distance metric. In the case of Levenshtein, the measurement of 'closeness' is in terms of the number of insertions and deletions required to turn one string into another. Other common textual similarity metrics include n-grams and phonetic distance ("Soundex"). In other example embodiments, all service descriptors are classified by textual similarity. Performing classification according to national billing code equivalents substantially increases the accuracy and number of service descriptors grouped. For procedures having corresponding preferred national billing codes, the disclosed embodiments will classify service descriptors to their preferred national billing code equivalent. By using a textual similarity metric, service descriptors can be attached to one another based on similarity. The process of grouping service descriptors, without a national billing code equivalent, includes calculating the distance according to at least one textual similarity metric (in this case Jaccard distance, i.e. a metric that measures how dissimilar two sets are) between one unattached service descriptor and all other unattached service descriptors, including those assigned to new service designations.

Attachment denotes that a service descriptor is in the set of service descriptors belonging to the same service. If the service designation does not exist, the service is then named and a numeric code is added. FIG. 14 depicts the process of adding a new procedure code. The new procedure code is represented in the example figure by a CPT code 202 assigned to a service descriptor 204 and price 206 for each health provider 218. In the example of FIG. 14 and elsewhere herein, health providers 214 are represented by pseudonyms such as "hospital Q", "hospital R", and so on. During operation of an embodiment 100 the correct names of institutions are stored and displayed. A threshold 'degree of confidence' must be met for the service descriptor to be attached to another service descriptor. The threshold 'degree of confidence' will preferably have a greater than 95% classification accuracy rate. The classification accuracy is determined by a human expert on a randomly-chosen subset. The human expert decides if the two service descriptors are the same procedure. Because of the 'degree of confidence' threshold, service descriptors can go unmatched.

An additional embodiment is to attach all service descriptors to national billing codes equivalents or to one another, using more than one textual similarity metric. In that embodiment, a matrix of weights would be used to combine textual similarity metrics together. As discussed previously, the textual similarity metrics could include Levenshtein distance, Jaccard distance, N-grams and Soundex. The weights for the textual similarity metrics would be created from training classified data, i.e. service descriptors grouped by human experts (for no 'appropriate' national billing code equivalent) or from chargemasters with 'appropriate' national billing code equivalents. For attachment, of service descriptors to national billing code equivalents the threshold 'degree of confidence' would be greater than 95% accuracy either from grouping from human experts or from chargemasters with 'appropriate' national billing code equivalents.

Figure 15:
FIG. 15 depicts how service descriptors are grouped for comparison of a simple 'glucose test' under CPT code 82947.

On a healthcare consumer-friendly price comparison interface 26, prices for a health service can be viewed, grouped and sorted from lowest to highest by users 28. Healthcare consumers can then find the facility with the lowest rates for a health service. For instance, when Hospital A has code 10021 with price $633 and Hospital B shows a service description of "fine needle anes" classified by an embodiment into code 10021 with price $1827, a user may compare prices with confidence even though the descriptors are dissimilar to a person unfamiliar with chargemasters. The output of the system and method allows users to compare the price for the service descriptor with a national billing code equivalent from Hospital B to the same service at Hospital A. Auxiliary information can also be included like the Centers of Medicare and Medicaid Services health provider ratings, the safety protocol, and the patient experience. FIG. 15 shows the results of this process for a simple glucose test, illustrating for each health provider 218 a service descriptor 204, a new service designation 226 enabling price comparisons for comparable services between different providers resulting from operation of the embodiment 100, and a price 206. FIG. 16 shows an example healthcare consumer price comparison interface 26 with health provider pricing information for two selected health providers, identified in the example figure by pseudonyms "ABC Medical Foundation" and "XYZ Imaging".

Figure 17:
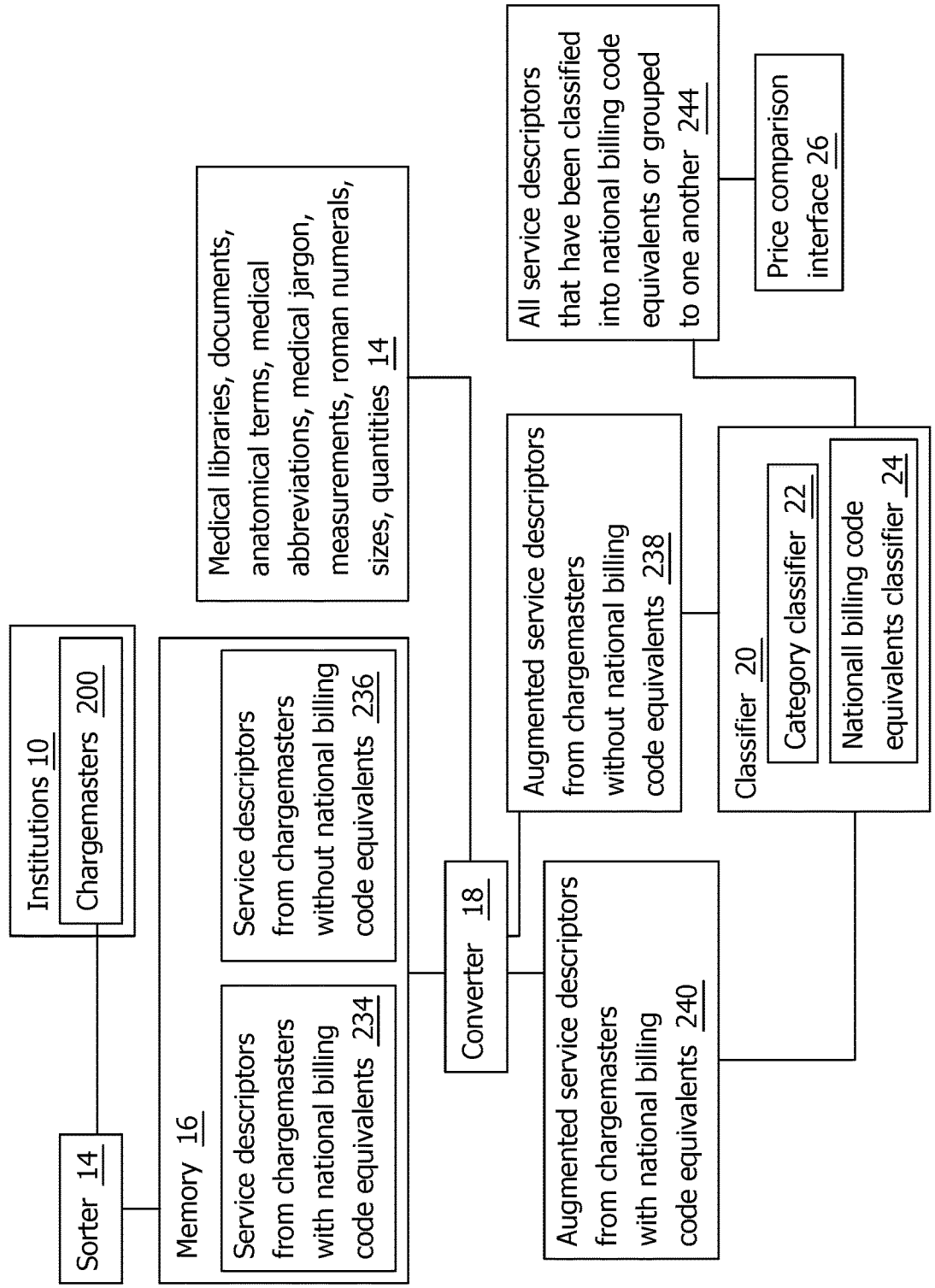
FIG. 17 is a schematic diagram of how data flows in the system and method of classifying and grouping service descriptors to compare health provider prices.

In the preferred embodiment, the computer processor 102 is configured to perform operations including, but not limited to: accessing chargemasters from machine-readable public data stores from institutions 10 through an intervening computer network 104, in a sorter 12 in data communication with the processor 102, sorting the chargemasters by whether they have included national billing code equivalents, attaching medical terms, jargon, abbreviations with medical libraries 14 to augment terms in descriptors stored in memory 16, building a preprocessed and extended service descriptor terms processed through the converter 18, training a supervised two-stage classifier 20 with service descriptors that have attached national billing code equivalents, which includes classification to a category 22 and then classification to a national billing code equivalent 24, classifying new service descriptors, which have no attached national billing code equivalents, with the two-stage classification model; if category classification 22 found 'no CPT', then the service descriptor is grouped based on textual similarity, and aggregating health provider prices by billing codes (for both service descriptors classified into national billing code equivalents and new designations of service descriptors) in a computer interface 26 to be viewed by users 28. FIG. 17 is a schematic diagram for an example embodiment 100 illustrating example data flows performed under the direction of the computer processor 102. FIG. 17 further illustrates examples of service descriptor processing by an embodiment 100, including sorting of chargemasters 200 into service descriptors 234 from chargemasters with national billing code equivalents and service descriptors 236 from chargemasters without national billing code equivalents, augmented service descriptors 238 from chargemasters without national billing code equivalents, augmented service descriptors 240 from chargemasters with national billing code equivalents, and all service descriptors 244 that have been classified into national billing code equivalents and/or grouped to one another. Augmented service descriptors 240 from chargemasters with national billing code equivalents may be used to train 242 the classifier 20.

Another example embodiment 100 uses an ensemble of classification models to attach service descriptors into national billing code equivalents. More than one model can be used in conjunction to improve classification accuracy. An aggregation rule could be used to then select the national billing code equivalent from the results of multiple models. An example of an aggregation rule is the most common predicted national billing code equivalent is attached.

In the embodiments 100 herein, service descriptors 204 are attached to national billing code equivalents 212 or to one another by textual similarity metric(s). Once service descriptors have been attached to a national billing code equivalent or grouped by textual similarity metric(s), a comprehensive listing of procedures provided by all American health providers can be created. The listing includes services that are attached to national billing code equivalents and services that are not attached to national billing code equivalents, but are offered at more than one health provider and are described by each health provider with sufficient textual similarity.

The disclosed example embodiments provide for comparison of health provider prices for medical services. Embodiments provide price comparability and greater transparency for health provider services, enabling patients and caregivers to price compare and choose the health provider with the lowest prices for most services, medications, medical devices and fees offered at health providers in the United States.

What is claimed is:

1. A computer-implemented method, comprising:

forming a comprehensive list of services provided by a plurality of health providers, the comprehensive list formed from a plurality of chargemasters received in a machine-readable format from each of the health providers, the chargemaster from each of the health providers including a plurality of service descriptors and corresponding prices represented as a plurality of character strings, each of the character strings corresponding to a healthcare service from one of the health providers having a different sequence of characters from a character string for the same healthcare service from another health provider, and modifying the service descriptor from each health provider into an augmented service descriptor in the comprehensive list representing a same healthcare service from each health provider, the modifying including:

storing, in a memory of a computer processor, the plurality of chargemasters, each of the plurality of chargemasters from a different health provider;

operating the computer processor to sort with a first set of input rules the plurality of chargemasters into a group of chargemasters including billing code equivalents and a group of chargemasters without billing code equivalents;

operating the computer processor to sort the group of chargemasters including billing code equivalents into a subgroup with an appropriate national billing code equivalent for each of a plurality of service descriptors and another subgroup without an appropriate national billing code equivalent for each of a plurality of service descriptors;

with the computer processor, applying a plurality of preprocessing rules to modify service descriptors from each chargemaster into the augmented service descriptors, the plurality of preprocessing rules including:
extending abbreviations into complete words;
replacing words with synonyms;
removing stopwords specific to each health provider; and
replacing numbers with equivalent text;
training a text-based classifier operated by the computer processor with the service descriptors from the group of chargemasters with national billing code equivalents;
classifying, with the trained text-based classifier, the service descriptors from the group of chargemasters without a national billing code equivalent into a national billing code equivalent;
applying a textual similarity metric to all the service descriptors without a national billing code equivalent, forming a group of service descriptors having a textual similarity above a selected threshold degree of confidence, and assigning a corresponding national billing code equivalent to the group of service descriptors in the comprehensive list;
receiving a request for a price comparison between the health providers for a healthcare service; and
displaying the national billing code equivalent, the augmented service descriptor, and the price from each of the health providers for the requested healthcare service retrieved from the comprehensive list, the comprehensive list having augmented service descriptors each formed with a higher accuracy and/or a higher consistency than expected for a classification of service descriptors by a human expert.

2. The computer-implemented method of claim 1, wherein the classifying into a national billing code equivalent is performed when the classifying is above a threshold degree of confidence.

3. The computer-implemented method of claim 1, wherein the subgroup with an appropriate national billing code equivalent includes the chargemasters having specifications corresponding to national billing code equivalents.

4. The computer-implemented method of claim 1, further comprising classifying words selected from the service descriptors in each of the chargemasters into a word type according to character-by-character equivalence of the selected words and a list of words for each of the word types.

5. The computer-assisted method of claim 1, wherein the classifying with the trained text-based classifier of service descriptors from the group of chargemasters without a national billing code equivalent further includes a variable importance factor, the variable importance factor preferentially selecting words, frequencies of words, and types of words most likely to occur in a selected national billing code equivalent.

6. The computer-assisted method of claim 1, further comprising the calculation of a match score, and for a match score above a threshold degree of confidence, classifying the service descriptor into a national billing code equivalent.

7. The computer-assisted method of claim 1, further comprising ranking national billing codes applicable to a service descriptor in order of probability.

8. The computer-assisted method of claim 1, wherein the forming a group of service descriptors having textual similarity further comprises ordering the service descriptors according to a probability of each service descriptor being attached to a national billing code equivalent.

9. The computer-assisted method of claim 1, further comprising:
selecting at least one additional textual similarity metric;
selecting a weighting factor for each of the textual similarity metrics; and
combing the textual similarity metrics according to the weighting factors.

10. The computer-assisted method of claim 1, wherein a model for classifying service descriptors with national billing code equivalents includes a loss function.

11. The computer-assisted method of claim 10, wherein the model comprises an ensemble of classification models, each of the classification models in the ensemble trained on a selected chargemaster service descriptor.

12. The computer-assisted method of claim 1, further comprising forming a listing of services offered by health providers from the group of service descriptors having textual similarity above the selected threshold degree of confidence and an assigned national billing code equivalent.

* * * * *